US005776686A

United States Patent [19]

Smith et al.

[11] Patent Number: 5,776,686

[45] Date of Patent: Jul. 7, 1998

[54] **DEVELOPMENT OF A PCR-BASED METHOD FOR IDENTIFICATION OF *TILLETIA INDICA*, CAUSAL AGENT OF KARNAL BUNT OF WHEAT**

[75] Inventors: Oney P. Smith, Frederick; Gary L. Peterson, Walkersville; Raymond J. Beck, Frederick; Morris R. Bonde, Middletown; Norman W. Schaad, Myersville, all of Md.

[73] Assignee: The United States of America as represented by the Secretary of Agriculture, Washington, D.C.

[21] Appl. No.: 772,961

[22] Filed: Dec. 24, 1996

Related U.S. Application Data

[60] Provisional application No. 60/009,439, Dec. 29, 1995.

[51] Int. Cl.[6] .............................. C12Q 1/68; C07H 21/02; C07H 21/04; C12N 15/00

[52] U.S. Cl. .............................. 435/6; 536/23.1; 536/24.3; 935/76; 935/77; 935/78

[58] Field of Search .............................. 435/6; 536/23.1, 536/24.3; 935/76, 77, 78

[56] References Cited

U.S. PATENT DOCUMENTS 4,965,188 10/1990 Mullis et al. .............................. 436/6

OTHER PUBLICATIONS

Armour et al., Human Molecular Genetics 3(43): 599–605 (Mar. 1994).

Genbank Accession No. X75409.

Ferreira et al., Phytopathology 85(10): Abstract No. 490, p. 1175 (1995).

Smith et al., Phytopathology 84(10): Abstract No. 679, p. 1152 (1994).

Bej et al. Critical Reviews in Biochemnistry and Molecular Biology 26(3/4) :301–334 (1991).

Steffan et al., Annual Reviews in Microbiology 45 : 137–161(1991).

*Primary Examiner*—W. Gary Jones

*Assistant Examiner*—Ethan Whisenant

*Attorney, Agent, or Firm*—M. Howard Silverstein; Randall E. Deck; John D. Fado

[57] ABSTRACT

The polymerase chain reaction (PCR) was used to identify *Tilletia indica*, the causal agent of Karnal bunt of wheat. The method uses two sets of oligonucleotide primers developed by sequence analysis of cloned Dra I fragments of mitochondrial DNA of *T. indica*. The primer pair TI17M1 (5'-TCCCCTTGGATCAGAACGTA-3') and TI17M2 (5'-AGAAGTCTAACTCCCCCCTCT-3'), derived from clone pTI-MD17, amplified a single 825-bp product from all isolates of *T. indica* and no products for other Tilletia species. In addition, the primer pair TI57M1 (5'-TTTTCCCTCTCTC-CTTTTTTCA-3') and TI57M2 (5'-AGCAAAGACAAAGTAGGCTTCC-3'), derived from clone pTI-MD57, produced a product of 118 bp which was unique to *T. indica*.

18 Claims, No Drawings

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

-continued ( i i i ) HYPOTHETICAL: NO ( i v ) ANTI-SENSE: NO ( v i ) ORIGINAL SOURCE:
( A ) ORGANISM: Tilletia indica
( C ) INDIVIDUAL ISOLATE: Pantanagar- 91
( I ) ORGANELLE: Mitochondrion ( v i i ) IMMEDIATE SOURCE:
( B ) CLONE: pTI-MD17

( x i ) SEQUENCE DESCRIPTION: SEQ ID NO:1:

TCCCCTTGGA TCAGAACGTA 20

( 2 ) INFORMATION FOR SEQ ID NO:2:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Tilletia indica
( C ) INDIVIDUAL ISOLATE: Pantanagar- 91
( I ) ORGANELLE: Mitochondrion ( v i i ) IMMEDIATE SOURCE:
( B ) CLONE: pTI-MD17

( x i ) SEQUENCE DESCRIPTION: SEQ ID NO:2:

AGAAGTCTAA CTCCCCCCTC T 21

( 2 ) INFORMATION FOR SEQ ID NO:3:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Tilletia indica
( C ) INDIVIDUAL ISOLATE: Pantanagar- 91
( I ) ORGANELLE: Mitochondrion ( v i i ) IMMEDIATE SOURCE:
( B ) CLONE: pTI-MD57

( x i ) SEQUENCE DESCRIPTION: SEQ ID NO:3:

TTTTCCCTCT CTCCTTTTTT CA 22

( 2 ) INFORMATION FOR SEQ ID NO:4:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

-continued ( i i i ) HYPOTHETICAL: NO ( i v ) ANTI-SENSE: NO ( v i ) ORIGINAL SOURCE:
( A ) ORGANISM: Tilletia indica
( C ) INDIVIDUAL ISOLATE: Pantanagar- 91
( I ) ORGANELLE: Mitochondrion ( v i i ) IMMEDIATE SOURCE:
( B ) CLONE: pTI-MD57

( x i ) SEQUENCE DESCRIPTION: SEQ ID NO:4:

AGCAAAGACA AAGTAGGCTT CC 22

DEVELOPMENT OF A PCR-BASED METHOD FOR IDENTIFICATION OF *TILLETIA INDICA*, CAUSAL AGENT OF KARNAL BUNT OF WHEAT

CROSS REFERENCE TO RELATED APPLICATIONS

This application hereby claims the benefit of U.S. provisional patent application Ser. No. 60/009,439, filed Dec. 29, 1995, the contents of which are incorporated by reference herein.

BACKGROUND OF THE INVENTION

1. Field of the Invention

The invention relates to novel oligonucleotide sequences which may be used as primers for the identification of *Tilletia indica* by polymerase chain reaction (PCR) assays.

2. Description of the Prior Art

*Tilletia indica* Mitra is a fungal plant pathogen that causes Karnal bunt of wheat (*Triticum aestivum* L.) (13). This nonsystemic smut pathogen is spread by airborne sporidia at the time of flowering. The resulting infection leads to partial bunting of wheat kernels and a characteristic fish-like odor which emanates from infected grain (19). The major impact of the disease is on wheat quality and not yield reduction (3).

Karnal bunt is found in several tropical and subtropical areas of the world, including India (13) and Mexico (10). The disease has not been reported in the U.S. (15); however, due to several interceptions of teliospores in wheat shipments entering the U.S. from Mexico (10), it has become a significant concern to the U.S. wheat industry and U.S. Department of Agriculture (USDA).

The movement of wheat into the U.S. and other Karnal bunt-free countries is the subject of strict quarantine regulations (15). A major problem encountered with the identification of *T. indica*-contaminated wheat shipments is that at least one other smut pathogen produces teliospores that are morphologically similar. This non-quarantined pathogen, *T. barclayana* (Bref.) Sacc. and Syd., is the causal agent of kernel smut of rice (*Oryza sativa* L.). Teliospores of *T. barclayana* often contaminate wheat shipments because wheat transport systems, harvesting equipment, and storage facilities also process rice. In a recent survey of U.S. wheat export samples in southern ports, 8% of the composite samples taken from 308 ships were contaminated with *T. barclayana* teliospores (Peterson et al, unpublished data). Presently, isozyme analysis is used to distinguish isolates of *T. indica* from *T. barclayana* using proteins extracted from germinated teliospores; however, this method requires considerable experience with interpretation of complex isozyme polymorphisms associated with these species (1,2). For these reasons, isozyme analysis is not considered a practical approach for the routine identification of *T. indica*.

SUMMARY OF THE INVENTION

We have now discovered two pairs of novel oligonucleotide primers for distinguishing *Tilletia indica* from *T. barclayana* by polymerase chain reaction (PCR) (14). These primers specifically amplify DNA fragments unique to *T. indica*; the DNA fragments are not amplified from any other Tilletia species. The presence of *T. indica* in biological samples, particularly grains such as wheat, may be detected by PCR using either or both pairs of the disclosed primers. The primers may also be incorporated into kits for the detection and identification of *T. indica*.

In accordance with this discovery, it is an object of this invention to provide novel oligonucleotides as primers for PCR assays for the specific detection and identification of *T. indica*.

It is also an object of this invention to provide PCR assay methods using the primers for the detection and identification of *T. indica*.

Other objects and advantages of this invention will become readily apparent from the ensuing description.

DETAILED DESCRIPTION OF THE INVENTION

The oligonucleotide primers of this invention were developed by sequence analysis of cloned DraI fragments of mitochondrial DNA of *Tilletia indica*. The primers comprising the first pair have been designated TI17M1 and TI17M2, and have the following DNA sequences: 5'-TCCCCTTGGATCAGAACGTA-3' (SEQ ID NO. 1) and 5'-AGAAGTCTAACTCCCCCCTCT-3' (SEQ ID NO. 2), respectively. Primers TI17M1 (SEQ ID NO. 1) and TI17M2 (SEQ.ID. NO. 2) generate an 825 bp amplification product from all isolates of *T. indica*, but they do not amplify DNA from other Tilletia species. The primers comprising the second pair have been designated TI57M1 and TI57M2, and have the following DNA sequences: 5'-TTTTCCCTCTCTCCTTTTTTCA-3' (SEQ ID NO. 3) and 5'-AGCAAAGACAAAGTAGGCTTCC-3' (SEQ ID NO. 4), respectively. In contrast to the first mentioned pair of primers, primers TI57M1 (SEQ ID NO. 3) and TI57M2 (SEQ ID NO.4) generate an 118 bp amplification product, as well as a minor product with an estimated size of 410 bp. However, like the 825 bp product, the 118 bp product generated by primers TI57M1 and TI57M2 (SEQ ID NO.4) is unique to *T. indica* and is not produced from other Tilletia species.

In accordance with the preferred embodiment, optimal results have been obtained using primers which are identical in length and DNA sequence to the above described primers TI17M1 (SEQ ID NO.1) and TI17M2 (SEQ ID NO.2), and/or TI57M1 (SEQ ID NO.3) and TI57M2 (SEQ ID NO.4). However, the practitioner skilled in the art will recognize that the length of the primers used may vary. For example, it is envisioned that shorter primers containing at least 17 consecutive bases of the nucleotide sequences of these primers (i.e. TI17M1 (SEQ ID NO.1) and TI17M2 (SEQ ID NO.2), and/or TI57M1 (SEQ ID NO.3) and TI57M2SEQ ID NO.4) may be suitable. Non-complementary nucleotide fragments may also be attached to the 5' end of the primers, effectively increasing their length. The exact upper limit of the length of the primers is not critical. However, typically the primers will be less than or equal to approximately 50 bases, preferably less than or equal to 30 bases. Further still, the bases included in the primers may be modified as is conventional in the art, including but not limited to incorporating detectable labels such as biotin or fluorescent labels.

Detection of *T. indica* is generally accomplished by amplifying the DNA from a test sample by polymerase chain reaction and assaying for the presence of the above-mentioned amplification products. DNA for the amplification process may be prepared by lysing the cell wall of fungi present in the collected samples, extracting, and collecting the released DNA. While it is envisioned that crude cell lysate may be used, the skilled practitioner will recognize that any non-DNA material present in the sample may interfere with the polymerase reaction or subsequent analysis. The actual method of sample preparation will also vary with the structure or stage of development of the target fungi. For instance, without being limited thereto, when assaying samples of teliospores, the spores are preferably crushed and lysed, such as by grinding and suspension in cell lysis buffer, followed by digestion with proteinase and RNase. When assaying samples of mycelia, the cell wall is preferably lysed such as by freezing and grinding, and the DNA extracted using conventional techniques. Alternatively, a direct PCR could be used without extracting DNA such as a hot start protocol recognized in the art.

Prior to cell lysis and DNA extraction, the sample of microorganisms may be subjected to an optional preliminary step of culturing (biological amplification) in order to expand the number of microorganisms and remove inhibitors. Although the PCR assay is sufficiently sensitive that such a preliminary step is not essential, as a practical matter, reliability is enhanced and sensitivity is increased when very low numbers of microorganisms are assayed. Preliminary culture of the sample is preferably employed when assaying samples containing less than about 1,000 teliospores, particularly those containing less 10 teliospores. Culture may be conducted using techniques conventional in the art, including but not limited to culture in potato dextrose broth.

Amplification is carried out according to conventional procedures in the art, such as described by Mullis (U.S. Pat. No. 4,683,202), the contents of which are incorporated by reference herein. Generally, PCR is conducted in a reaction mixture comprising a suitable buffer, such as 10 mM Tris-HCl, pH 8.3, 50 mM KCl, 1.5 mM $M_2Cl_2$, 0.001 wt/vol gelatin. The reaction mixture also comprises the template DNA, the DNA polymerase, one or both pairs of the primers described above, and an ample amount of each of the four deoxynucleoside triphosphates (dATP, dCTP, dGTP, and TTP). The amount of polymerase must be sufficient to promote DNA synthesis throughout the predetermined number of amplification cycles. Guidelines as to the actual amount of polymerase are generally provided by the supplier of the PCR reagents and are otherwise readily determinable by a person of ordinary skill in the art. The amount of each primer must be in substantial excess of the amount of target DNA to be amplified. The amount of primer needed for the reaction mixture can be estimated in terms of the ultimate number of amplified fragments desired at the conclusion of the reaction.

To prevent false positive or negative results, the skilled practitioner will recognize that the assays should include controls as is conventional in the art. For instance, suitable negative controls may contain no primer or no DNA (i.e. "water controls"), as well as DNA from a closely related microorganism such as *T. barclayana*. Positive controls may contain DNA from known *T. indica* samples. Positive control assays are also preferably conducted using suitable universal PCR primers, such as ITS3 and ITS4 described by White et al., [1990, Amplification and direct sequencing of fungal ribosomal RNA genes for phylogenetics, In: Innis et al., (Eds.), PCR Protocols, Academic Press, San Diego, pp. 315–322, the contents of which are incorporated by reference herein].

The reaction mixture is preferably overlaid with a mineral oil or the like for the purpose of preventing evaporation of the medium and undesired increases in the concentrations of the reagents during the course of the reaction. The first step of the reaction involves heating the mixture to melt the DNA; that is, to denature double-stranded configuration to two single-stranded templates. Using as an example Taq polymerase, the denaturing is typically conducted at a temperature in the range of about 90°–96° C. for about 1–2 min. The second step of the cycle is a cooling to about 35°65° C., and preferably 50°–60° C., for about 1–3 min to permit annealing of the primers to the template. In the third step, the mixture is held within the temperature range of about 70°–75° C. for about 2–4 min to allow for primer extension by the polymerase. This cycle is usually repeated approximately 20–30 times in order to achieve the desired amplification of the target sequence. Eventually amplification reaches a plateau as the proportion of reagents to products diminishes. In general, it is recognized that continuing amplification significantly beyond 30 cycles may introduce abnormalities. Of course it is understood that the conditions set forth herein are merely exemplary, and optimization of the conditions for any given PCR would be within the purview of the person in the art. Additional detail regarding PCR is given by Arnhelm et al. [C&EN, pages 36–47 (Oct. 1, 1990)], herein incorporated by reference.

At the conclusion of the amplification reaction, either of both of the 825 bp or 118 bp amplified products may be detected using techniques conventional in the art. In the preferred embodiment, the amplification products are conveniently visualized by gel electrophoresis and ethidium bromide staining in comparison with preestablished standards. Alternative techniques for the detection of the amplification products include Southern or dot-blot hybridization techniques utilizing DNA sequences internal to the oligonucleotide primers.

The oligonucleotide primers of this invention may be prepared using any conventional DNA synthesis method, such as, phosphotriester methods such as described by Narang et al. (1979, Meth. Enzymol., 68:90) or Itakura (U.S. Pat. No. 4,356,270), or and phosphodiester methods such as described by Brown et al. (1979, Meth. Enzymol., 68:109), or automated embodiments thereof, as described by Mullis et al. (U.S. Pat. No. 4,683,202). In one such automated embodiment diethylphosphoramidites are used as starting materials and may be synthesized as described by Beaucage et al., Tetrahedron Letters (1981), 22:1859–1862. One method for synthesizing oligonucleotides on a modified solid support is described in U.S. Pat. No. 4,458,066, the contents of which are incorporated by reference herein. It is also possible to use a primer which has been isolated from a biological source (such as a restriction endonuclease digest).

The oligonucleotide primers may be used to detect *T. indica* obtained from virtually any source. However, in the preferred embodiment, the primers are particularly advantageous for the detection of *T. indica* on grains, most particularly wheat. Fungal samples may be collected using techniques known in the art, such as washing followed by filtration or centrifugation, brushing, or scraping. Using a seed wash extraction method for infested grain samples followed by PCR testing of germinated teliospores, *T. indica* can be reliably detected at a level of 5 teliospores per 50-g grain sample.

As mentioned hereinabove, the primers may be incorporated into a convenient kit for detecting *T. indica*. The kit should contain at least one pair of TI17M1 (SEQ ID NO.1) and TI17M2 (SEQ ID NO.2), or TI57M1 (SEQ ID NO.3) and TI57M2 (SEQ ID NO.4), although both pairs may be included for added flexibility and reliability.

The following examples are intended only to further illustrate the invention and are not intended to limit the scope of the invention which is defined by the claims.

EXAMPLES

The primers and assay disclosed hereinbelow are described by Smith et al. (1996, Phytopathology, 86:115–122) the contents of which are incorporated by reference herein.

Materials and Methods

Fungal isolates and DNA extraction. Seventy-eight isolates derived from 32 separate field collections of *T. indica* were tested. Of these, 10 isolates were each composed of a mixture of germinated teliospores from a single collection, 51 from single-teliospore, and 17 from single-basidiospore isolations. Seventeen field collections of *T. barclayana* were the source for 69 isolates, including four isolates each composed of a mixture of germinated teliospores from a single collection, and 65 single-teliospore isolates. In addition, two isolates of *T. tritici* (Bjerk.) Wint., one of *T. laevis* Kuhn, four of *T. controversa* Kuhn, and three of *T. fusca* Ellis and Everhart were also included in the studies. The identities of all teliospore collections of *T. indica* used in this study were confirmed by pathogenicity on the highly susceptible wheat cultivar WL-711. Plant inoculations were performed as described by Warham et al. (20). The identity of many of the *T. barclayana* collections was confirmed on the rice cultivar Blue Bonnet by the same inoculation method. Although pathogenicity results are not available for some isolates of *T. barclayana*, their identities were determined by morphological characteristics, place of origin, host from which first isolated, and the presence of a pink-red pigment that is often, but not always, produced by this organism in culture (22). A list of collections used in this study is presented in Table 1. All pathogen manipulations were conducted in the containment laboratory at Frederick, Md. (12). Mycelial cultures were maintained on potato dextrose agar plates at 18° C. Mycelial plugs were transferred to 2% water agar to induce the production of abundant secondary sporidia. These sporulating cultures were transferred to shaker culture (200 RPM), grown at room temperature (21°–23° C.) for 5 to 7 days in 200 ml of yeast malt extract broth (Difco, Detroit, Mich.), collected by gravity filtration on Miracloth (Calbiochem, La Jolla, Calif.), and stored at −70° C. prior to freeze drying. Total DNA was extracted from 1 g of freeze-dried mycelium as described by Crownhurst et al. (5). Mitochondrial DNA (mtDNA) was isolated from total DNA of one isolate of *T. indica* (Pantanagar-91), and one isolate of *T. barclayana* (CA-1) by cesium chloride-bis-benzimide gradient ultracentrifugation as described by Karlovsky and deCock (9). DNA concentrations were determined by UV spectroscopy at 260 nm (16).

Southern-blot analysis of mitochondrial DNA. Mitochondrial DNA (0.5 μg) from *T. indica* (Pantanagar-91) and *T. barclayana* (CA-1) was incubated for 4 hr at 37° C. with 10 units of Dra I in 20 μl. Fragments were resolved in a 1.2% agarose gel using 0.5×TBE buffer, stained with ethidium bromide, and photographed (1×TBE is 89 mM Tris-borate, 89 mM boric acid, 2 mM EDTA, pH 8.3). The agarose gel was alkaline blotted to a Zeta-Probe GT membrane (Bio-Rad, Richmond, Calif.), prehybridized, hybridized, and washed as described by the manufacturer. One microgram of *T. barclayana* mtDNA (CA-1) was radiolabeled by random priming (Ready-To-Go Kit, Pharamica, Piscataway, N.J.) using [a-32P]dCTP (3000 Ci/mmole) (Amersham Corp., Arlington Heights, Ill.) and added to the hybridization solution to a final concentration of $1\times10^6$ cpm/ml. Autoradiography was performed at −70° C. for 3 days with intensifying screens.

Recombinant DNA techniques. *T. indica* mtDNA was cleaved with Dra I and cloned into the Sma I site of the plasmid vector pBLUESCRIPT II SK+(Stratagene, La Jolla, Calif.) using DH5a host cells and standard recombinant DNA techniques (16). Ampicillin-resistant transformants were subjected to blue/white screening, and the size of inserts from 80 white colonies was determined by PCR (7) using T7 and T3 primers (GIBCO BRL, Gaithersburg, Md.) which flank the multiple cloning site of the vector. Selected recombinant clones were grown by standard protocols (16) and plasmid DNA was isolated using a Qiagen Plasmid Midi Kit (Qiagen Inc., Chatsworth, Calif.). Plasmid DNA was sequenced using the Sequenase Kit (United States Biochemical Corp., Cleveland, Ohio) and T3 or T7 primers. Alternatively, plasmid DNA was sequenced using a Prism Ready Reaction DyeDeoxy Terminator Cycle Sequencing Kit and a Model 373A DNA Sequencing System (Applied Biosystems, Inc., Foster City, Calif.). The resulting data were analyzed using the sequence analysis software package (version 7.0) of the Genetics Computer Group (6). The program PRIMER (version 0.5) (Whitehead Institute/MIT, Cambridge, Mass.) was used to assist with the selection of PCR primer pairs from DNA sequence data. Primers were synthesized commercially (Genosys Biotechnologies, Inc., The Woodlands, Tex.).

PCR method. Amplification reactions contained 10 mM Tris-HCl, pH 8.3, 50 mM KCl, 1.5 mM MgCl2, 10 μg/ml gelatin, 200 μM each dNTP, 1 μM each primer, 25 ng DNA, 1.25 units Taq DNA polymerase (Perkin-Elmer, Norwalk, Conn.) in a final volume of 50 μl. After overlaying the reaction mixture with 50 μl mineral oil, amplifications were performed in a Perkin-Elmer Thermal Cycler 480. Samples were first heated at 94° C. for 3 min, followed by 30 cycles of denaturation at 94° C. for 1 min, annealing at 60° C. for 1 min, and extension at 72° C. for 2 min. A final step at 72° C. for 5 min was added to complete primer extension. In addition, using these same conditions, control PCR assays were conducted using the primers ITS3 and ITS4. These primers anneal to conserved binding sites and amplify an internal transcribed spacer (ITS) region of ribosomal DNA for several different fungi (21). Products greater than 400 bp were analyzed using 1.2% agarose gels in TAE buffer (40 mM Tris-acetate, pH 8.0, 1 mM EDTA) followed by staining with ethidium bromide. Smaller products were analyzed using pre-cast 20% acrylamide gels (NOVEX, San Diego, Calif.) in 1×TBE buffer followed by staining with ethidium bromide.

Post PCR Southern-blot analysis. Agarose gels were blotted to MagnaGraph nylon membranes (Micron Separations, Inc., Westboro, Mass.) using standard methodology (16). Polyacrylamide gels were electroblotted to NOVEX Nylon+ membranes (NOVEX, San Diego, Calif.) for 2 h at 25 V as described by the manufacturer. Blots were prehybridized at 68° C. for 2 h in 10 ml of 2× prehybridization/hybridization solution (GIBCO BRL) and hybridization was conducted for 12 h at 68° C. in 10 ml of prehybridization/ hybridization solution containing $1\times10^6$ cpm/ml of $^{32}$P-labeled plasmid DNA. Probes were prepared by random priming as described above. Blots were washed twice at room temperature for 15 min in 2×SSC, 0.1% SDS then twice at 68° C. in 0.1×SSC, 0.1%SDS followed by auto-radiography at −70° C. for 6–72 h using an intensifying screen (1×SSC is 0.15M NaCl, 0.015M sodium citrate, pH 7.0).

PCR assay of ungerminated teliospores from infected seed. Teliospore DNA was extracted using a Puregene DNA Isolation Kit (Gentra Systems, Inc., Research Triangle Park, N.C.) with modifications. Briefly, dry teliospores obtained from sori were hand crushed between two siliconized glass slides and the debris suspended in 80 μl cell lysis buffer (CLB). After transfer to a 1.5 ml microfuge tube containing 80 µl CLB, 1 µl proteinase K (20 mg/ml) was added followed by incubation at 55° C. for 1 h. After addition of 1 µl RNase A (4 mg/ml) and incubation at 37° C. for 15 min, 50 µl protein precipitation solution was added and DNA was recovered following instructions of the manufacturer. The final teliospore DNA pellet was suspended in 20 µl TE buffer (10 mM Tris, pH 8.0, 1 mM EDTA). The PCR assay was conducted as described above using 4 µl aliquots of each teliospore DNA solution. Teliospore amounts tested were 10,000, 5,000, 1,000, 500, 100, and 10 spores per slide as estimated by light microscope counting. Three collections of *T. indica* teliospores (MX-81, MX-91, Pakistan) and one of *T. barclayana* (Arkansas) were tested.

Seed wash extraction of infested grain samples and PCR assay of germinated teliospores. Grain samples (50 g) were suspended in 100 ml distilled water containing 1–2 drops Tween 20 (Sigma, St. Louis, Mo.). The suspension was poured through a 10-cm diameter, 52-µm, Spectra/Mesh Nylon Filter (Spectrum, Inc., Houston, Tex.). After washing twice with 100 ml distilled water, the filtrate was poured through a 10-cm diameter, 20-µm Spectra/Mesh Nylon Filter. The 20-µm filter was washed twice with 100 ml of distilled water and the debris was rinsed off the filter using 10 ml of distilled water and transferred to a 15 ml conical centrifuge tube. After incubation overnight at 20 C, samples were centrifuged for 3 min (200×g). The pellets were suspended in 10 ml 0.525% sodium hypochlorite and immediately centrifuged for 1 min (1000×g). The pellets were suspended in 10 ml sterile distilled water and centrifuged 3 min (200×g) to wash the debris. This step was repeated and pellets were suspended in 500 µl sterile distilled water.

Each 500-µl suspension was transferred to a 2% water agar (Difco, Detroit, Mich.) plate containing 100 mg each of ampicillin and streptomycin sulfate followed by incubation at 20° C. (12 h light). After 6–10 days, one or more blocks of agar (ca. 1 cm2), each containing a germinated teliospore, were cut from the plate and transferred to the inside surface of the cover of a 100×15-mm petri plate (one agar block per plate). The bottom of the petri plate contained 10 ml of sterile potato dextrose broth (Difco). After 2–3 days, a floating mycelial matte (0.5–1.0 cm diameter) was produced from basidiospores and secondary sporidia that were deposited on the surface of the broth from the germinated teliospore.

The mycelial matte was removed by needle, touched to a piece of filter paper to remove excess media, and transferred to a 1.8 ml cryovial. The sample was frozen in liquid nitrogen and hand pulverized using a precooled glass rod (8-mm diameter). DNA was extracted using a Puregene Isolation Kit and 150 µl total CLB as described above. The final DNA pellet was suspended in 50 µl TE and 1 µl aliquots were used for PCR as described above.

The sensitivity of the seed wash extraction method was determined by artificial infestation of 50-g wheat grain samples. The amounts of *T. indica* teliospores artificially added were 0, 1, 2, 5, and 10 teliospores per 50-g wheat sample. Five replicates were conducted for each level of artificial teliospore infestation.

Results

Pathogenicity testing and morphological identification. All collections of *T. indica* infected the wheat cultivar WL-711. Collections of *T. barclayana* from the Philippines, Washington, Arkansas, California, and Texas produced disease in the rice cultivar Blue Bonnet. Collections of *T. barclayana* from China, Brazil, and India were obtained directly from infected rice, a non-host for *T. indica* (15,19), and satisfied the basic morphological criteria for *T. barclayana* (22). The remaining collections of *T. barclayana* were isolated from U.S. grain elevators in Texas from wheat of U.S. origin and evaluated morphologically. Isolates SL-7C, SL-10B, SL-11A, R-1 TX Comp, and TM-6C did not produce pink-red pigment when cultured on potato dextrose agar (22).

Selection of cloned Dra I fragments of *T. indica* mtDNA and primers. Clones containing inserts between 0.6 and 2.0-kbp were chosen for further analysis. Clones were selected as candidates for *T. indica*-specific sequences because Southern-blot analysis indicated that $^{32}$P-labeled mtDNA from *T. barclayana* did not hybridize to the majority of Dra I restriction fragments of *T. indica* mtDNA in this size range (data not shown). One clone, designated pTI-MD17, and containing a 1.1-kbp insert, was partially sequenced and used for computer-assisted primer selection. Primer TI17M1 (SEQ ID NO.1) (5'-TCCCCTTGGATCAGAACGTA-3') and Primer TI17M2 (SEQ.ID. NO. 2) (5'-AGAAGTCTAACTCCCCCCTCT-3') amplified an 825-bp product using plasmid pTI-MD17 as template (data not shown). Analysis of a second clone, designated pTI-MD57 and containing a 0.9-kbp insert, resulted in the selection of Primer TI57M1 (SEQ ID NO.3) (5'-TTTTCCCTCTCTCCTTTTTTCA-3') and Primer TI57M2 (SEQ ID NO.4) (5'-AGCAAAGACAAAGTAGGCTTCC-3'). Using plasmid pTI-MD57, this primer pair yielded the predicted amplification product (118 bp) and an additional minor product with an estimated size of 410 bp (data not shown).

Amplification of mycelial DNA samples and specificity of mtDNA-derived primers. As summarized in Table 1, the primer pair TI17M1 (SEQ ID NO.1) and TI17M2 (SEQ ID NO. 2) produced a 825-bp product for all isolates of *T. indica*. Attempts to amplify DNA from isolates of *T. barclayana* and four additional Tilletia species produced negative results (Table 1). As summarized in Table 1, similar analyses using the primer pair TI57M1 (SEQ ID NO.3) and TI57M2 (SEQ ID NO.4) demonstrated a 118-bp product that was specific for *T. indica*. In addition to the expected 118-bp product, a minor product with an estimated size of 410 bp was observed using these primers. This minor product was not unique to *T. indica* as determined by post-PCR hybridization analysis (see below). The results of testing the primers ITS3 and ITS4 demonstrated that all species and isolates of Tilletia produced a 420-bp product (Table 1).

Post-PCR hybridization analysis. The specificity of the amplification products produced by both pairs of mtDNA-derived primers from *T. indica* was evaluated by Southern-blot analysis for all isolates tested. Probe pTI-MD17 hybridized to the 825-bp product amplified from *T. indica* isolates, but not to products from *T. barclayana* or three additional Tilletia species. Similar results were obtained with probe pTI-MD57 and its 118-bp product for *T. indica, T. barclayana* and other Tilletia species (data not shown). In repeated Southern-blot hybridization experiments using probe pTI-MD57, a faint autoradiographic signal corresponding to the 410-bp product was detected for other Tilletia species, including nine isolates of *T. barclayana*; however, hybridization to the 118-bp product was not observed (data not shown).

Application of PCR assay to identify ungerminated teliospores. The primers TI17M1 (SEQ ID NO.1) and TI17M2 (SEQ ID NO.2) amplified the expected 825-bp product from DNA extracted from 10,000, 5,000, or 1,000 teliospores and the amount of product was proportional to the number of teliospores processed (data not shown). The PCR product was not detected using DNA extracted from 500 or fewer teliospores of *T. indica* (Data not shown) and was not observed for DNA extracted from 10,000 teliospores of *T. barclayana* (data not shown).

Application of PCR assay to identify germinated teliospores extracted and germinated from grain samples. The results of testing teliospores extracted and germinated from naturally infested grain samples are summarized in Table 2. Both pairs of PCR primers readily identified *T. indica* from four grain samples. Similar assays conducted on grain samples infested with *T. barclayana* yielded negative results (Table 2).

To estimate the sensitivity of the method for recovering and identifying germinated teliospores, grain samples (50 g) artificially infested with 10, 5, 2, 1, or 0 teliospores were tested. As summarized in Table 3, germinated teliospores were recovered and positively identified by PCR for all samples infested with 5 or 10 teliospores. Some samples infested with 1 or 2 teliospores were not identified by PCR because germinated teliospores were not recovered (Table 3).

Discussion

Our results show that *T. indica* can be readily distinguished from *T. barclayana* and other Tilletia species using PCR and the primer pair TI17M1 (SEQ ID NO.1) and TI17M2 (SEQ ID NO.2). This primer pair generates an 825-bp product that is specific to *T. indica*. The successful use of ITS primers to amplify a ribosomal DNA spacer element from all the fungal isolates indicates that the negative results obtained with *T. barclayana* and other Tilletia species were not associated with DNA degradation or the presence of PCR inhibitors. Additional tests conducted with the primer pair TI57M1 (SEQ ID NO.3) and TI57M2 (SEQ ID NO.4) demonstrated amplification of a 118-bp product which was unique to *T. indica*. The primers TI57M1 (SEQ ID NO.3) and TI57M2 (SEQ ID NO.4) produced a minor fragment (410 bp) which was not unique to *T. indica* based on southern-blot hybridization analysis. These results indicate that the primer binding sites for the 410-bp product are present in other Tilletia species, including *T. barclayana*. Amplification of the 410-bp product, using the plasmid pTI-MD57 as template, indicates these sites are present on the cloned mtDNA fragment.

Although teliospores of *T. tritici*, *T. laevis*, *T controversa* and *T. fusca* are morphologically distinct from *T. indica* and *T. barclayana*, they were included in our studies to confirm primer specificity because they are common contaminants found in grain shipments. For example, in 1991 we surveyed 308 wheat export shipments from U.S. southern ports and found that 38% of the ships were contaminated with *T. tritici* (Peterson and Bonde, unpublished data). In terms of the practical applications of our seed wash extraction and teliospore germination methodology, *T. tritici* and *T. laevis* would frequently be recovered with *T. indica* and *T. barclayana* because they share common germination requirements (18,19,22). In contrast, germinated teliospores of *T. controversa* and *T. fusca* would not be recovered because these species require colder temperatures and longer incubation periods for germination (11,18).

Our testing of ungerminated teliospores obtained from sori demonstrated that approximately 1,000 teliospores are preferred for optimal reliability of identification by PCR. This level of sensitivity is not adequate for practical applications which require the detection of *T. indica* in grain samples containing 10 or fewer teliospores. In order to satisfy this requirement, we developed an approach that uses teliospores germinated from a seed wash extraction of infested grain followed by PCR testing. We have successfully applied this methodology to the identification of *T. indica* in grain samples (Table 2) and have demonstrated that the detection sensitivity level approximates 5 teliospores per 50-g grain sample (Table 3).

In comparison to the complex polymorphisms associated with isozymes, which can be difficult to interpret (1), the PCR assay described here is easier to interpret because it is based on the presence or absence of single amplified product. We believe that the application of this method will be useful in international trade. The U.S. does not currently screen wheat exports for the presence of Karnal bunt teliospores because the disease has not been reported in the U.S. However, the PCR-based method may indeed prove useful in disputes over the identity of teliospores found in U.S. grain exports or in confirming the presence of *T. indica* in foreign grain imports. The identification of *T. indica* in a grain shipment could have a serious economic impact on the supplier and therefore test results may require second party confirmation. An advantage of our assay method is the ability to establish a viable reference culture from the original germinated teliospore. Furthermore, if Karnal bunt were found in the U.S., the PCR-based assay could be utilized for monitoring the distribution of the pathogen. This information would be useful in establishing quarantine areas and preventing the contamination of clean U.S. wheat shipments with teliospores from infested grain.

It is understood that the foregoing detailed description is given merely by way of illustration and that modifications and variations may be made therein without departing from the spirit and scope of the invention.

TABLE 1

Fungal isolates and results of PCR testing using two pairs of *T. indica*-derived primers and a control primer pair that amplify a ribosomal DNA sequence present in all species.

| Isolates Tested | Sample Comp.[a] | Origin/Year | Source | Collection Identification Method[b] | *T. indica*-derived Primers T117M1/2 | *T. indica*-derived Primers T157M1/2 | Control Primers ITS3/4 |
|---|---|---|---|---|---|---|---|
| *Tilletia indica* | | | | | | | |
| MX-81A, MX-81B | T | Mexico, 1981 | 1 | P | + | + | + |
| D3 | T | Mexico, 1981 | 1 | P | + | + | + |
| D3-S1, D3-S2, D3-S3, D3-S4 | B | Mexico, 1981 | 1 | P | + | + | + |
| CIANO 1982 | T | Mexico, 1982 | 2 | P | + | + | + |
| MX-82 pop | C | Mexico, 1982 | 1 | P | + | + | + |
| CIANO 1985 | C | Mexico, 1985 | 1 | P | + | + | + |
| CIANO 1986 | C | Mexico, 1986 | 1 | P | + | + | + |

TABLE 1-continued

Fungal isolates and results of PCR testing using two pairs of *T. indica*-derived primers and a control primer pair that amplify a ribosomal DNA sequence present in all species.

| Isolates Tested | Sample Comp.[a] | Origin/Year | Source | Collection Identification Method[b] | *T. indica*-derived Primers T117M1/2 | *T. indica*-derived Primers T157M1/2 | Control Primers ITS3/4 |
|---|---|---|---|---|---|---|---|
| Mall 1A, Mall 1B, Mall 1C | T | Mexico, 1986 | 1 | P | + | + | + |
| MX-87 | C | Mexico, 1987 | 1 | P | + | + | + |
| MX-87A, MX-87B | T | Mexico, 1987 | 1 | P | + | + | + |
| MX-88A, MX-88B, MX-88C | T | Mexico, 1988 | 1 | P | + | + | + |
| Fuente-1A, Fuente-1C | T | Mexico, 1989 | 1 | P | + | + | + |
| Mall-1A, Mall-1C | T | Mexico, 1989 | 1 | P | + | + | + |
| Navajoa 1A | T | Mexico, 1989 | 1 | P | + | + | + |
| Navajoa-pop | C | Mexico, 1989 | 1 | P | + | + | + |
| Yaqui-3B, Yaqui-3C, Yaqui-3D | T | Mexico, 1989 | 1 | P | + | + | + |
| MX-91A, MX-91B, MX-91C | T | Mexico, 1991 | 3 | P | + | + | + |
| Toluca pop | C | Mexico, 1991 | 4 | P | + | + | + |
| Toluca-1A, Toluca-1B | T | Mexico, 1991 | 4 | P | + | + | + |
| S-9A, S-9B, S-9C, S-6197A, S-6197B, S-6917C, S-6197D, S-6210A, S-6210B, S-6210C, S-6210D, S-6210E | T | Mexico, 1993 | 1 | P | + | + | + |
| Amritsar 1562 | C | India, 1983 | 5 | P | + | + | + |
| Sangar-83 pop | C | India, 1983 | 5 | P | + | + | + |
| Sangar-1A | T | India, 1983 | 5 | P | + | + | + |
| HD-2008A, HD-2288A, Punjab WL-711, Sample IIA, Sample IIB, TL-419A, WL 2265A | T | India, 1989 | 5 | P | + | + | + |
| Pantanagar-91, A-pop | C | India, 1991 | 6 | P | + | + | + |
| A3 | T | India, 1991 | 6 | P | + | + | + |
| A1-S1, A1-S2, A1-S3, A1-S4, A1-S5, A4-S2, A4-S3, A4-S4 | B | India, 1991 | 6 | P | + | + | + |
| B4 | T | Pakistan, 1985 | 7 | P | + | + | + |
| B3-S1, B4-S2, B4-S3, B4-S4, B4-S5 | B | Pakistan, 1985 | 7 | P | + | + | + |
| B-pop | C | Pakistan, 1985 | 7 | P | + | + | + |
| BZ-1, BZ-5 | T | Brazil, intercept* | 4 | P | + | + | + |
| Calexico CF1, Calex. CF2, Calex. CF3, Calex. CF4 | T | 1984 intercept from Mexico** | 8 | P | + | + | + |
| Calexico RR1 | T | 1983 Rail Car from Mexico** | 8 | P | + | + | + |
| *T. barclayana* | | | | | | | |
| CA-1, CA-2, CA-3, CA-4, CA-5, CA-6, CA-7 | T | California, 1985 | 9 | P | − | − | + |
| Wash-5, Wash-7, WAT-T01, WAT-T07, WAT-T12 | T | Washington, 1985 | 1 | P | − | − | + |
| AK-pop | C | Arkansas, 1986 | 7 | P | − | − | + |
| AK-T01, AK-T02, AK-T03 AK-T04, AK-T07, AK-T08 AK-T09 | T | Arkansas, 1986 | 7 | P | − | − | + |
| Cross T1, Cross T2, Miss. T1, Miss. T3, Loudon T1, Loudon T2, Ark T1, Ark T2, Ark T3 | T | Arkansas, 1993 | 10 | P | − | − | + |
| R-1 TX Comp | C | Galveston, TX, 1991 | 9 | M | − | − | + |
| SL-7C, SL-7D, SL-7E, SL-10B SL-11A | T | Galveston, TX, 1991 | 11 | M | − | − | + |
| Tb TX-11, Tb TX-12, | T | Galveston, TX, 1991 | 3 | P | − | − | + |
| 63212F, 63335, 63335 | T | Galveston, TX, 1991 | 3 | M | − | − | + |
| TM-6C | T | Galveston, TX, 1991 | 9 | M | − | − | + |
| 55457Fa, 55486L | T | Beaumont, TX, 1991 | 3 | M | − | − | + |
| TS-137a, TS-139all, TS 140a | U | Brazil, 1991 | 12 | S | − | − | + |
| Philip-1, Philip-2, Philip-3, Philip-4, Philip-5, Philip-6, Philip-7, TbP-T01, TbP-T02, TbP-T04, TbP-T05, TbP-T07 TbP-T08 | T | Philippines, 1989 | 13 | P | − | − | + |
| TbP-pop | C | Philippines, 1989 | 13 | P | | | |
| PRC 1990 | C | China, 1990 | 14 | S | − | − | + |
| PRC 1991 | C | China, 1991 | 15 | S | − | − | + |
| PJ-T03, PJ-T06, PJ-T07, PJ-T12, PJ-T13, PJ-T14 | T | China, 1991 | 15 | S | − | − | + |
| IND-90A, IND-90E | T | India, 1990 | 5 | S | − | − | + |
| IND-91A, IND-91C, IND-91B | T | India, 1991 | 6 | S | − | − | + |

TABLE 1-continued

Fungal isolates and results of PCR testing using two pairs of *T. indica*-derived primers and a control primer pair that amplify a ribosomal DNA sequence present in all species.

| Isolates Tested | Sample Comp.[a] | Origin/Year | Source | Collection Identification Method[b] | *T. indica*-derived Primers T117M1/2 | T157M1/2 | Control Primers ITS3/4 |
|---|---|---|---|---|---|---|---|
| *T. controversa* | | | | | | | |
| D-107 | C | Craigmont, ID, 1989 | 16 | P | – | – | + |
| D-131 | C | Creston, MT, 1989 | 16 | P | – | – | + |
| D-035 | C | Ontario, Canada, 1989 | 17 | S | – | – | + |
| D-046 | C | Czechoslovakia, 1989 | 18 | S | – | – | + |
| *T. tritici* | | | | | | | |
| C-100 | C | Pullman, WA, 1990 | 16 | P | – | – | + |
| C-125 | C | Cavendish, ID, 1990 | 16 | P | – | – | + |
| *T. laevis* | | | | | | | |
| F-008 | C | Stillwater, OK, 1989 | 19 | S | – | – | + |
| *T. fusca* | | | | | | | |
| G-105 | C | Boise, ID, 1990 | 20 | S | – | – | + |
| G-110 | C | Flora, OR, 1990 | 20 | S | – | – | + |
| G-112 | C | Logan, UT, 1990 | 20 | S | – | – | + |
| Seed wash[c] | | | | | | | |
| SW-1 | C | Belle Chase, LA | 3 | NA | – | – | + |
| SW-2 | C | Beaumont, TX | 3 | NA | – | – | + |

[a]C = isolate derived from mycella grown from a composite of germinating teliospores; T = isolate from the isolation of a single teliospore. B = isolate from a single basidiospore.; U = Unknown composition.
[b]P = identity confirmed by host inoculation, M = identity based on morphology and origin, S = identity based on collection from infected host and morphology
[c]DNA isolated from a composite of miscellaneous fungi (no *T. indica* or *T. barclayana* observed) extracted by a wheat seed wash of 50 g export wheat sample and grown in YM shake culture for 7 days.
*Quarantine interception by Empresa Brazileira de Pesquisa Agropecris (EMBRAPA)
**Quarantine interception by U.S. Animal and Plant Health Inspection Service (APHIS)
1. R. Kahn, USDA, APHIS, Hyattsville, MD; 2. G. Fuentes-Davila, CIMMYT, Mexico; 3. G. Peterson, USDA, ARS, Frederick, MD.; 4. I. Butler, CIMMYT, El Batan, Mexico; 5. K. Gill, Punjab Agric. Univ., Ludhiana, India; 6. M. Bonde, USDA, ARS, Frederick, MD.; 7. M. Royer, USDA, APHIS, BATTS, Hyattsville, MD; 8. T. Boratynski, APHIS, PPQ El Centro, CA; 9. T. Matsumoto, Calif. Dept. of Agric., Sacramento, CA; 10. I. Lee. Univ. of Arkansas, Fayettville, AK; 11. G. Urskin, USDA Federal Grain Inspection Service, Galveston, TX; 12. C. Castro, EMPRAPA, Plant Quarantine Service (CAPQ), Beijing, PRC; 15. J. Peng, CAPQ, Daltan, PRC; 16. B. Goates, USDA, ARS, Aberdeen, ID; 17. G. White, Plant Protection and Quarantine, Agriculture Canada, Ottawa, Canada; 18. R. Vyskumny, Plestany, CSSR; 19. I. Williams, Oklahoma State Univ., Stillwater, OK; 20. J. Hoffman, USDA, retired, Hanatel, HI.

TABLE 2

Results of testing naturally infested gram samples for *Tilletia indica* using the seed wash extraction method and polymerase chain reaction (PCR) assay of germinated teliospores

| Sample | Origin | Supplier[a] | Source[b] | Results of PCR: *T. indica* specific primers T117M1/2 | T157M1/2 | Control primers ITS3/4 | Alternate identification method[d] |
|---|---|---|---|---|---|---|---|
| *Tilletia indica* | | | | | | | |
| MX88 | Mexico, 1988 | 1 | W | 3/3 | 3/3 | 3/3 | P |
| Calexico CF | California intercept[e] | 2 | W | 5/5 | 5/5 | 5/5 | P |
| Mexicali RR | California rail car[e] | 2 | T | 1/1 | 1/1 | 1/1 | P |
| S-9 | Mexico, 1993 | 1 | W | 3/3 | 3/3 | 3/3 | P |
| *T. barclayana* | | | | | | | |
| Loundon Co. | Loundon Co., AR, 1994 | 3 | R | 0/1 | 0/1 | 0/1 | M |
| Cross Co. | Cross Co., AR, 1994 | 3 | R | 0/2 | 0/2 | 0/2 | M |
| Glen Co. | Glen Co., CA, 1985 | 4 | W | 0/3 | 0/3 | 0/3 | P |
| Philip | Philippines, 1989 | 5 | R | 0/5 | 0/5 | 5/5 | P |

[a]1.G. Fuentes-Davila, CIMMYT, Mexico; 2. T. Bottynski, APHIS, PPQ, El Centro, CA, 3. F Lee, Univ of Arkansas, AR; 5. T. Matsumoto, Calif Dept of Agric., Sacramento, CA; 6. J. Bonman, Int. Rice Res. Inst. Manila, Philippines.
[b]W = wheat; R = rice; and T = railroad box car.
[c]Denominator is number of germinated teliospores tested. Numerator is number testing positive by PCR
[d]P = identity confirmed by host inoculation; M = identity based on morphology/origin
[e]Quarantine interception from Mexico by U.S. Animal and Plant Health Inspection Service (APHIS).

TABLE 3

Results of testing the sensitivity of the seed wash extraction method showing number of germinated teliospores recovered from artifically infested wheat samples and identified as *Tilletia indica* by polymerase chain reaction (PCR)

| Replicate | Level of infestation[a] 0 | 1 | 2 | 5 | 10 |
|---|---|---|---|---|---|
| 1 | 0[b] | 1 | 1 | 3 | 10 |
| 2 | 0 | 0 | 0 | 3 | 6 |
| 3 | 0 | 1 | 2 | 4 | 6 |
| 4 | 0 | 0 | 0 | 5 | 6 |
| 5 | 0 | 0 | 0 | 4 | 5 |
| Frequency[c] | 0.0 | 40 | 40 | 100 | 100 |

[a]Number of teliospores of *T. indica* used to artifically infest a 50 g grain sample.
[b]Number of germinated teliospores recovered and positively identified as *T. indica* by PCS using primer pairs T117M1/M2 and T157M1/M2.
[d]Percentage of samples testing positive by PCR for the presence of *T. indica* teliospores.

LITERATURE CITED

1. Bonde, M. R., Peterson, G. L., and Matsumoto, T. T. 1989. The use of isozymes to identify teliospores of *Tilletia indica*. Phytopathology 79:596–599.
2. Bonde, M. R., Peterson, G. L., and Royer, M. H. 1988 Inheritance of isozymes in the smut pathogen *Tilletia indica*. Phytopathology 78:1276–1279.
3. Brennan, J. P., Warham E. J., Hernandez, J., Byerlee, D., and Coronel, F. 1990. Economic losses from Karnal bunt of wheat in Mexico. CIMMYT Economics Working Paper. Centro Internacional de Mejoramiento de Maiz y Trigo, El Batan, Mexico.
4. Commonwealth Mycological Institute. 1974. Distribution Maps of Plant Diseases, Nos. 75, 95, 173, and 294, 3rd ed. Commonwealth Agricultural Bureau, Kew, England.
5. Crownhurst, R. N., Hawthorne, B. T., Rikkerink, H. A., and Templeton, M. D. 1991. Differentiation of Fusarium solani f. sp. curcurbitae races 1 and 2 by random amplification of polymorphic DNA. Curr. Genet. 20:391–396.
6. Devereux, J., Haeberli, P., and Smithies, O. 1984. A comprehensive set of sequence analysis programs for the VAX. Nucleic Acids Res. 12:387–395.
7. Gussow, D., and Clackson, T. 1989. Direct clone characterization from plaques and colonies by polymerase chain reaction. Nucleic Acids Res. 17:4000.
8. Henson, J. M., and French, R. 1993. The polymerase chain reaction and plant disease diagnosis. Ann. Rev. Phytopathol. 31:81–109.
9. Karlovsky, P., and de Cock, A. W. 1991. Buoyant density of DNA-Hoechst 33258 (bisbenzimide) complexes in CsCl gradients: Hoechst 33258 binds to single AT base pairs. Anal. Biochem. 194:192–197.
10. Matsumoto, T. T., Boratynski, T. N., Showers, D. W., Higuera, D., and Luscher, D. 1984. Karnal bunt of wheat. Calif. Plt. Pest Dis. Rep. 3:45–47.
11. Meiners, J. P., Waldher, J. T. 1959 Factors affecting spore germination of twelve species of Tilletia from cereals and grasses. Phytopathology 49:724–728.
12. Melching, J. S., Bromfield, K. R., and Kingsolver, C. H. 1983. The plant pathogen containment facility at Frederick, Maryland. Plant Dis. 67:717–722.
13. Mitra, M. 1931. A new bunt of wheat in India. Ann. Appl. Biol. 18:178–179.
14. Mullis, K. B., and Faloona, F. A. 1989. Specific synthesis of DNA in vitro via a polymerase-catalyzed chain reaction. Methods Enzymol. 155:335–350.
15. Royer, M. H., and Rytter, J. 1988. Comparison of host ranges of *Tilletia indica* and *Tilletia barclayana*. Plant. Dis. 72:133–136.
16. Sambrook, J., Fritisch, E. F., and Maniatis, T. 1989. Molecular Cloning: A Laboratory Manual. 2nd Edition. Cold Spring Harbor Laboratory Press, Cold Spring Harbor, N.Y.
17. Smith, O. P., Peterson, G. L., Beck, R. J., Bonde, M. R., and Schaad, N. W. 1994. Development of a PCR-based assay to identify *Tilletia indica*, causal agent of Karnal bunt of wheat. Phytopathology (Abstr.) 80:1152.
18. Trione, E. J. 1982. Dwarf bunt of wheat and its importance in international wheat trade. Plant Dis. 66:1083–1088.
19. Warham, E. J. 1986. Karnal bunt disease of wheat: a literature review. Trop. Pest Manag. 32:229–242.
20. Warham, E. J., Mujeeb-Kazi, A., Rosas, V. 1986. Karnal bunt (*Tilletia indica*) resistance screening of Aegilops species and their practical utilization for *Triticum aestivum* improvement. Canadian J. of Plant Protection. 8:65–70.
21. White, T. J., Bruns, T., Lee, S., and Taylor, J. 1990. Amplification and direct sequencing of fungal ribosomal RNA genes for phylogenetics, pp. 315–322. In M. A. Innis, D. H. Gelfand, J. J. Sninsky, and T. J. White (Eds.), PCR Protocols. Academic Press, San Diego. 22. Whitney, N. G., and Frederiksen, F. A. 1975. Kernel smut of rice. Tex. Agric. Exp. Stn. Bull. MP 1231. 12 pp.

We claim:

1. An oligonucleotide primer comprising at least 17 consecutive bases of the DNA sequence 5'-TCCCCTTGGATCAGAACGTA-3' (SEQ ID NO. 1).

2. The oligonucleotide primer of claim 1 comprising the DNA sequence 5'-TCCCCTTGGATCAGAACGTA-3' (SEQ ID NO. 1).

3. An oligonucleotide primer comprising at least 17 consecutive bases of the DNA sequence 5'-AGAAGTCTAACTCCCCCCTCT-3' (SEQ ID NO. 2).

4. The oligonucleotide primer of claim 3 comprising the DNA sequence 5'-AGAAGTCTAACTCCCCCCTCT-3' (SEQ ID NO. 2).

5. An oligonucleotide primer comprising at least 17 consecutive bases of the DNA sequence 5'-TTTTCCCTCTCTCCTTTTTTCA-3' (SEQ ID NO. 3), wherein said primer consists of less than or equal to approximately 50 nucleotides.

6. The oligonucleotide primer of claim 5 comprising the DNA sequence 5'-TTTTCCCTCTCTCCTTTTTTCA-3' (SEQ ID NO. 3).

7. An oligonucleotide primer comprising at least 17 consecutive bases of the DNA sequence 5'-AGCAAAGACAAAGTAGGCTTCC-3' (SEQ ID NO. 4).

8. The oligonucleotide primer of claim 7 comprising the DNA sequence 5'-AGCAAAGACAAAGTAGGCTTCC-3' (SEQ ID NO. 4).

9. A set of oligonucleotide primers comprising a primer comprising at least 17 consecutive bases of the DNA sequence 5'-TCCCCTTGGATCAGAACGTA-3' (SEQ ID NO. 1) and a primer comprising at least 17 consecutive bases of the DNA sequence 5'-AGAAGTCTAACTCCCCCCTCT-3' (SEQ ID NO. 2).

10. The set of oligonucleotide primers of claim 9 comprising a primer comprising the DNA sequence 5'-TCCCCTTGGATCAGAACGTA-3' (SEQ ID NO. 1 and a primer comprising the DNA sequence 5'-AGAAGTCTAACTCCCCCCTCT-3' (SEQ ID NO. 2).

11. A set of oligonucleotide primers comprising a primer comprising at least 17 consecutive bases of the DNA sequence 5'-TTTTCCCTCTCTCCTCTTTTTTCA-3' (SEQ ID NO. 3) and a primer comprising at least 17 consecutive bases of the DNA sequence 5'-AGCAAAGACAAAGTAGGCTTCC-3' (SEQ ID NO. 4).

12. The set of oligonucleotide primers of claim 11 comprising a primer comprising the DNA sequence 5'-TTTTCCCTCTCTCCTTTTTTCA-3' (SEQ ID NO. 3) and a primer comprising the DNA sequence 5'-AGCAAAGACAAAGTAGGCTTCC-3' (SEQ ID NO. 4).

13. A method of detecting *Tilletia indica* in a sample comprising:

a. releasing DNA from a test sample;

b. amplifying said DNA with a pair of oligonucleotide primers selected from the group consisting of (i) primers comprising at least 17 consecutive bases of the DNA sequences 5'-TCCCCTTGGATCAGAACGTA-3' (SEQ ID NO. 1) and 5'-AGAAGTCTAACTCCCCCCTCT-3' (SEQ ID NO. 2), and (ii) primers comprising at least 17 consecutive bases of the DNA sequences 5'-TTTTCCCTCTCTCCTTTTTTCA-3' (SEQ ID NO. 3) and 5'-AGCAAAGACAAAGTAGGCTTCC-3' (SEQ ID NO. 4); and c. detecting the presence of amplified DNA.

14. The method as described in claim 13 wherein said sample comprises wheat.

15. The method as described in claim 13 wherein said pair of oligonucleotide primers comprises primers comprising the DNA sequences 5'-TCCCCTTGGATCAGAACGTA-3' (SEQ ID NO. 1) and 5'-AGAAGTCTAACTCCCCCCTCT-3' (SEQ ID NO. 2).

16. The method as described in claim 15 wherein said detecting comprises detecting an 825 bp amplified DNA product.

17. The method as described in claim 13 wherein said pair of oligonucleotide primers comprises primers comprising the DNA sequences 5'-TTTTCCCTCTCTCCTTTTTTCA-3' (SEQ ID NO. 3) and 5'-AGCAAAGACAAAGTAGGCTTCC-3' (SEQ ID NO. 4).

18. The method as described in claim 17 wherein said detecting comprises detecting one or both of an 118 bp amplified DNA product and an 410 bp amplified DNA product.

* * * * *